United States Patent [19]
Riedl et al.

[11] 3,932,754
[45] Jan. 13, 1976

[54] GAS ANALYZER

[75] Inventors: Max J. Riedl; Thaddeus C. Ross, both of Santa Barbara, Calif.

[73] Assignee: Infrared Industries, Inc., Santa Barbara, Calif.

[22] Filed: Mar. 27, 1974

[21] Appl. No.: 455,345

Related U.S. Application Data

[63] Continuation of Ser. No. 325,729, Jan. 22, 1973, abandoned.

[52] U.S. Cl. ................................................ 250/343
[51] Int. Cl.² ........................................... G01N 21/26
[58] Field of Search ............ 250/343, 344, 345, 346

[56] References Cited
UNITED STATES PATENTS

| | | | |
|---|---|---|---|
| 2,547,212 | 4/1951 | Jamison | 250/343 |
| 3,562,524 | 2/1971 | Moore | 250/343 |
| 3,649,833 | 3/1972 | Leaf | 250/343 |
| 3,677,652 | 7/1972 | Little | 250/343 |
| 3,696,247 | 10/1972 | McIntosh | 250/343 |

*Primary Examiner*—Craig E. Church
*Attorney, Agent, or Firm*—Dominik, Knechtel, Godula & Demeur

[57] ABSTRACT

A multiple gas analyzer is disclosed utilizing the infrared absorption principle for determining the quantity of two or more gases with a sample tube and a reference tube in parallel orientation with an infrared source between one end of the two tubes, and an infrared detector assembly between the other end of the tubes. Immediately opposed to each end of the tubes are a pair of mirrors, one being a transmitting mirror remote from the infrared source and directing the infrared beam in parallel paths through the reference tube and sample tube, and a receiving mirror opposite the infrared detector assembly to focus the infrared beam after passing through the tubes on to the infrared detectors. A chopper disc is interposed between the infrared source and the transmitting mirror to provide intermittently direct pulses to the infrared beam through the reference tube and sample tube to the infrared detectors, and a circuit is provided to compare the differential of signal strength from the two signals generated by each of the detectors and to calibrate the same with regard to the gas content being read. Filters are provided in the infrared detector assembly for that particular wave length in which the gas finds its signature for photon absorption. In the circuit, provision is made to first calibrate the unit for ambient variables, and thereafter to calibrate the unit against a factory determined span gas sample by means of vignetting the sample chamber to simulate a convenient up-scale reading of the particular gas being calibrated. Further adjustment is provided for comparing the high scale with the low scale in the course of sampling to thereby fully calibrate the unit and check the same during its operation.

9 Claims, 17 Drawing Figures

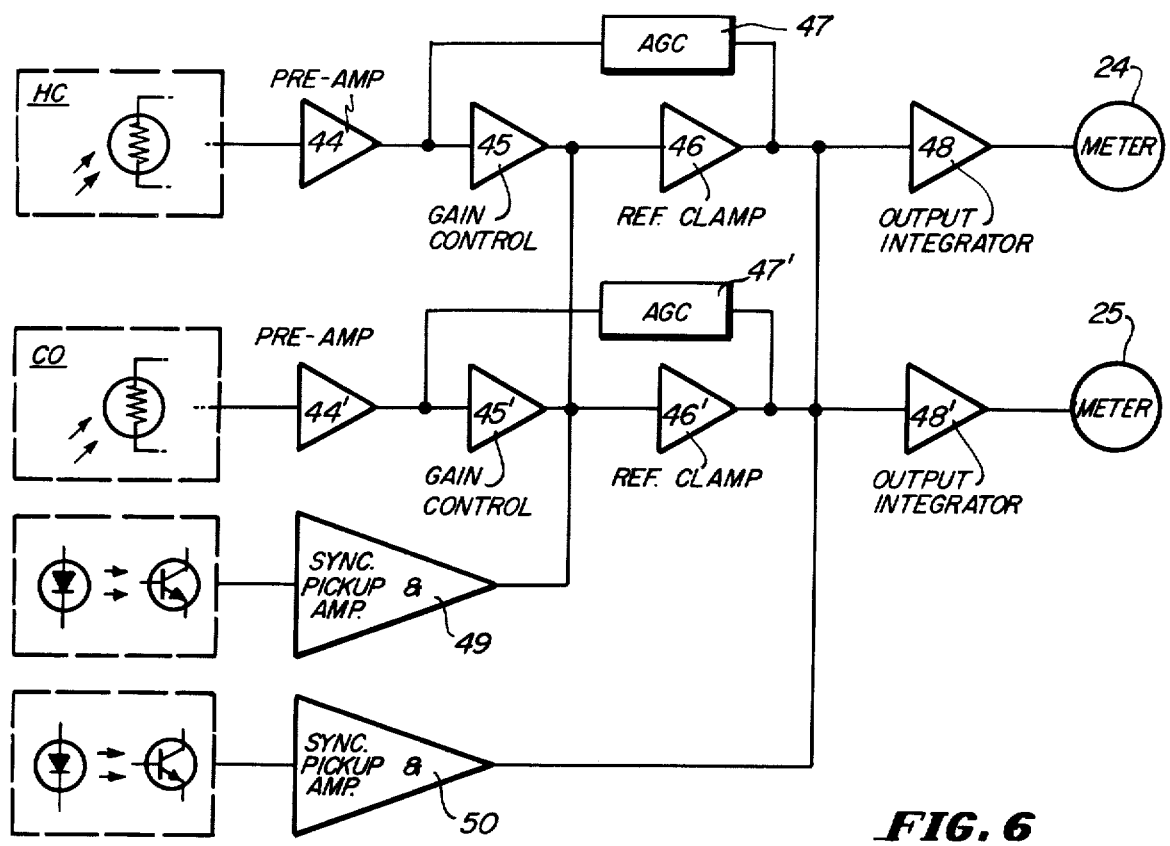
*FIG. 6*
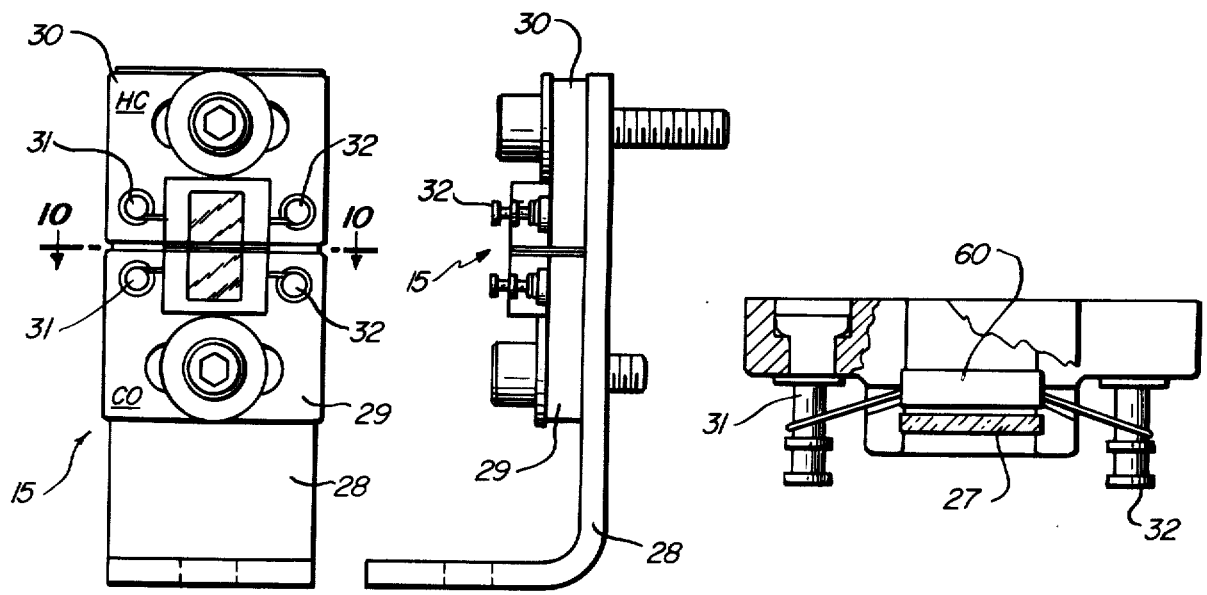
*FIG. 8*  *FIG. 9*  *FIG. 10*

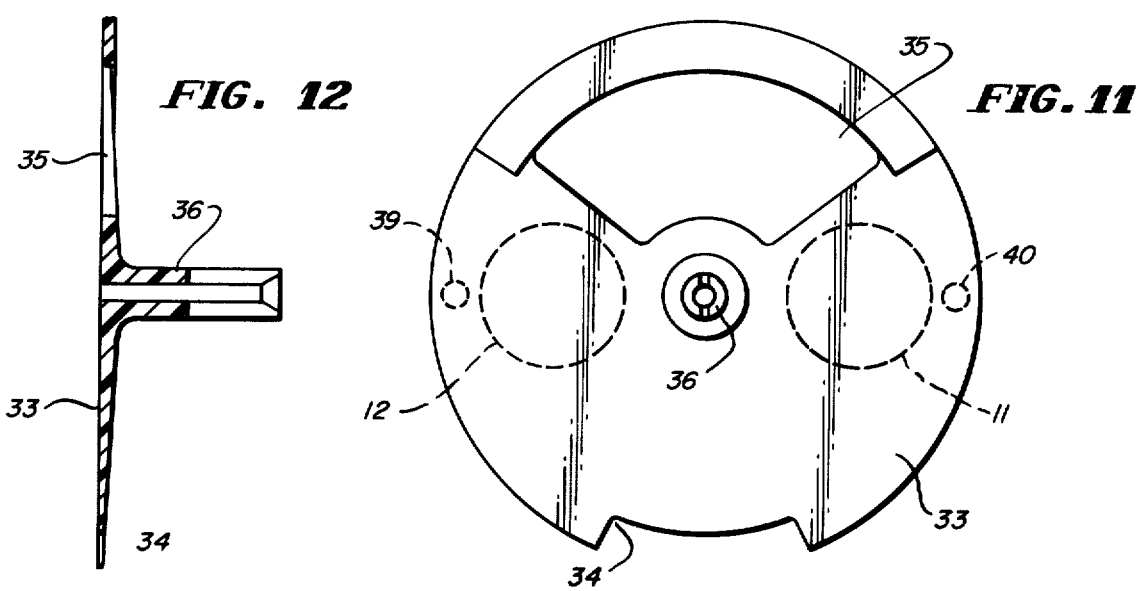
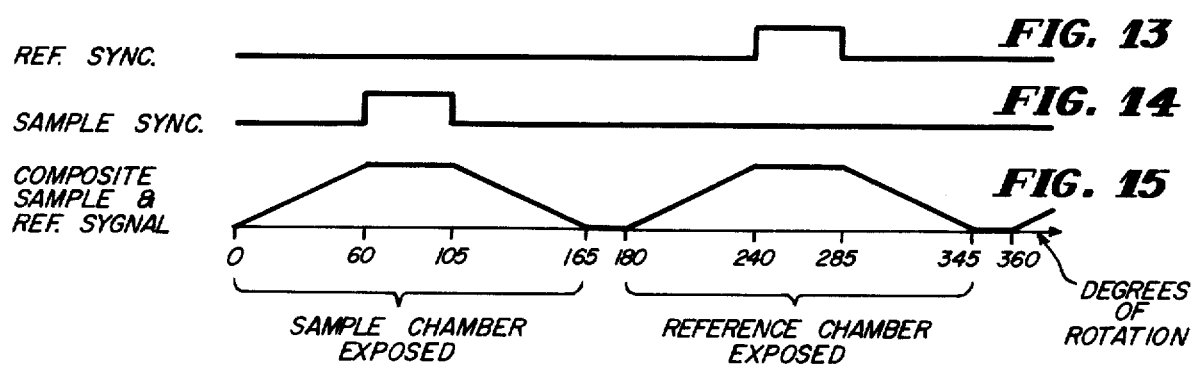

3,932,754

GAS ANALYZER

This is a continuation of application Ser. No. 325,729, filed Jan. 22, 1973, now abandoned.

BACKGROUND OF INVENTION

1. Field of Invention

The present invention relates to gas analyzers which operate on the principle that at a given wave length, photons are absorbed by a gas in direct proportion to its concentration. By transmitting infrared rays through a sample chamber and reading the same through a filtered detector, the drop in the output of the detector is calibrated to the concentration reading of the gas, such as carbon monoxide (CO) or unburned hydrocarbons (HC). Such instruments appear in Class 250, Subclass 43.5.

2. Description of Prior Art

The prior art is best set forth in Chapter 10 of Mullard, pages 129–142, the book title being:

*Applications of Infrared Detectors*, printed in 1971, by Wightman and Co., Ltd., London SW9 6DS, England
To be noted in particular with regard to the proposals made by Mullard, particularly on page 132, Figures A, B, and C, is the disclosure of a reference tube and a sample tube, and yet the discussion of a prototype beginning at page 136 relates only to a single tube unit. The problems encountered in the field, particularly in garages where temperature variables in cold weather can be between 70° and −40°C, illustrated the futility of using a single gas sample tube without a reference chamber. Furthermore, the unit shown is capable of reading for only one gas or ingredient at a time, whereas automotive emissions standards proposed require the simultaneous reading for CO and unburned HC since the two are to a degree interrelated in the adjustments required to reduce the concentration to acceptable levels. Where commercial units have been developed, such as illustrated in U.S. Pat. No. 3,562,522, they have been slow to warm up, such as one-half hour to an hour. In addition, continued variables have required almost constant tuning. Also lacking commercially is an inexpensive unit which will read out more than one gas or component simultaneously.

SUMMARY

A multiple gas analyzer employing the infrared absorption calibration technique is illustrated in the present invention, and includes a pair of parallel tubes, one a sample tube through which gas is pumped, and the other a reference tube in close parallel relationship to the sample tube which is filled with ambient air although it can be sealed and even reduced to a vacuum. An infrared source is positioned adjacent the two ends of one portion of the tubes, and a plurality of infrared detectors are fixedly positioned, with filter overlays, adjacent the other two ends of the tubes and therebetween. An opposed transmitting mirror concavely opposed to the infrared source reflects the infrared beams backwardly through the two tubes and on to a receiving concave mirror opposite the detectors. A chopper disc is provided between the infrared source and the transmitting mirror to alternatively deliver signals through the sample and reference tube to the detectors, the latter each being in circuit amplified relationship with a readout meter which compares the signal received by the detectors when passing through the sample chamber with the signal passing through the reference tube, and calibrating that differential to the concentration of the particular gas or gases being read. The circuit includes an amplifier, gain control, reference clamp, automatic gain control amplifier, and comparison means to direct a signal to a meter proportioned to the signal variation between the reference tube and sample tube signal. Multiple detector-filter combinations with parallel circuit and multiple meters permit the reading of two or more gas components simultaneously.

It is a particular object of the present invention to provide an accurate, reliable, fast starting, moderately priced gas analyzer which has particular value in reading exhaust gas pollutants and determining whether their level falls within certain limits. The subject analyzer can read two or more such pollutants simultaneously.

A more detailed object of the present invention but consonant with the objective set forth above is the provision of calibration adjustments which are not only reliable, but susceptible of operation by a semi-skilled person with brief training as to the calibration of the unit.

Still another advantage and objective of the present invention is to provide a gas analyzer which is lightweight, portable, and sufficiently temperature insensitive so that the same may be used out of doors or indoors in a garage or testing lane.

DESCRIPTION OF DRAWINGS

Further objects and advantages of the present invention will become apparent as the following description of an illustrative embodiment proceeds taken in conjunction with the accompanying drawings in which:

FIG. 6 is a schematic generally illustrating the circuit means of the gas analyzer;

FIGS. 8 and 9 are a front plan and a side plan view of the infrared detector assembly, respectively;

FIG. 10 is a sectional view taken along lines 10—10 of FIG. 8;

FIG. 11 is a front plan view of the chopper disc;

FIG. 12 is a sectional view taken along lines 12—12 of FIG. 11;

FIG. 13 illustrates the waveform of the reference sync pulse;

FIG. 14 illustrates the waveform of the sample sync pulse;

FIG. 15 illustrates the waveform of the composite sample and reference signal;

FIG. 16 is a front plan view of the calibration flag and motor assembly;

FIG. 17 is a side plan view, partially sectionalized, of the calibration flag and motor assembly.

Similar reference characters refer to similar parts throughout the several views of the drawings.

DESCRIPTION OF THE PREFERRED EMBODIMENT

Figure 2:
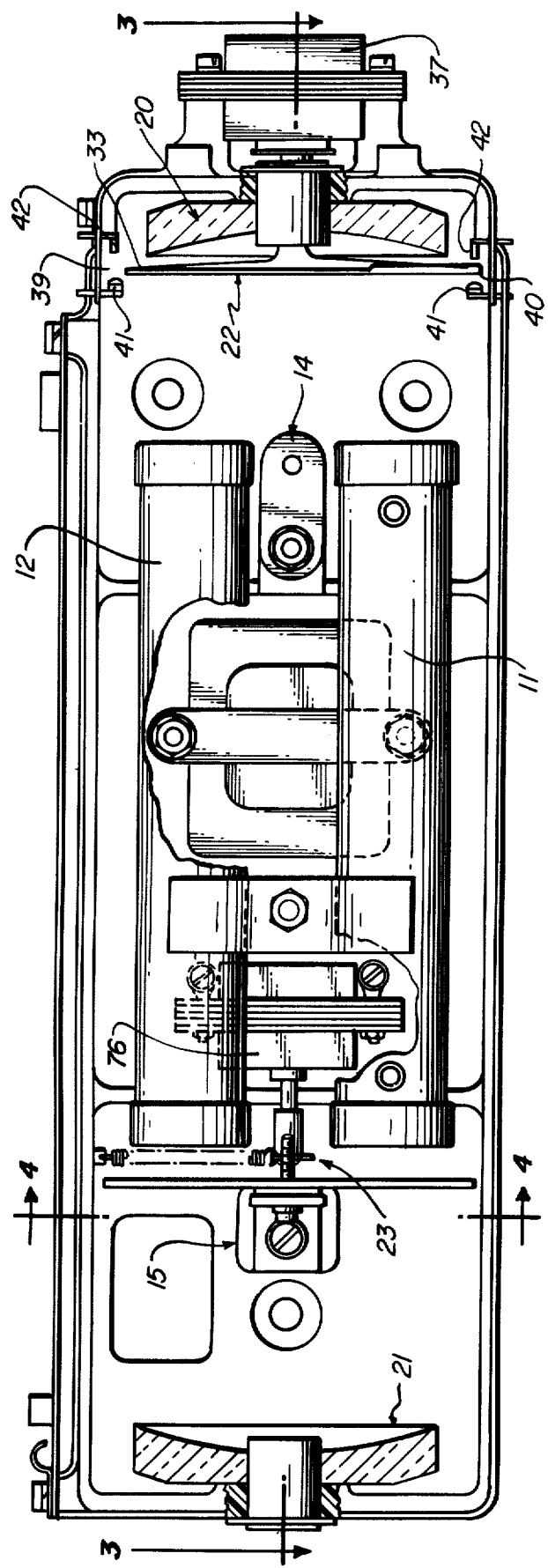
FIG. 2 is a top plan view, partially sectionalized and partially broken away, of the optical bench portion of the gas analyzer.
Figure 3:
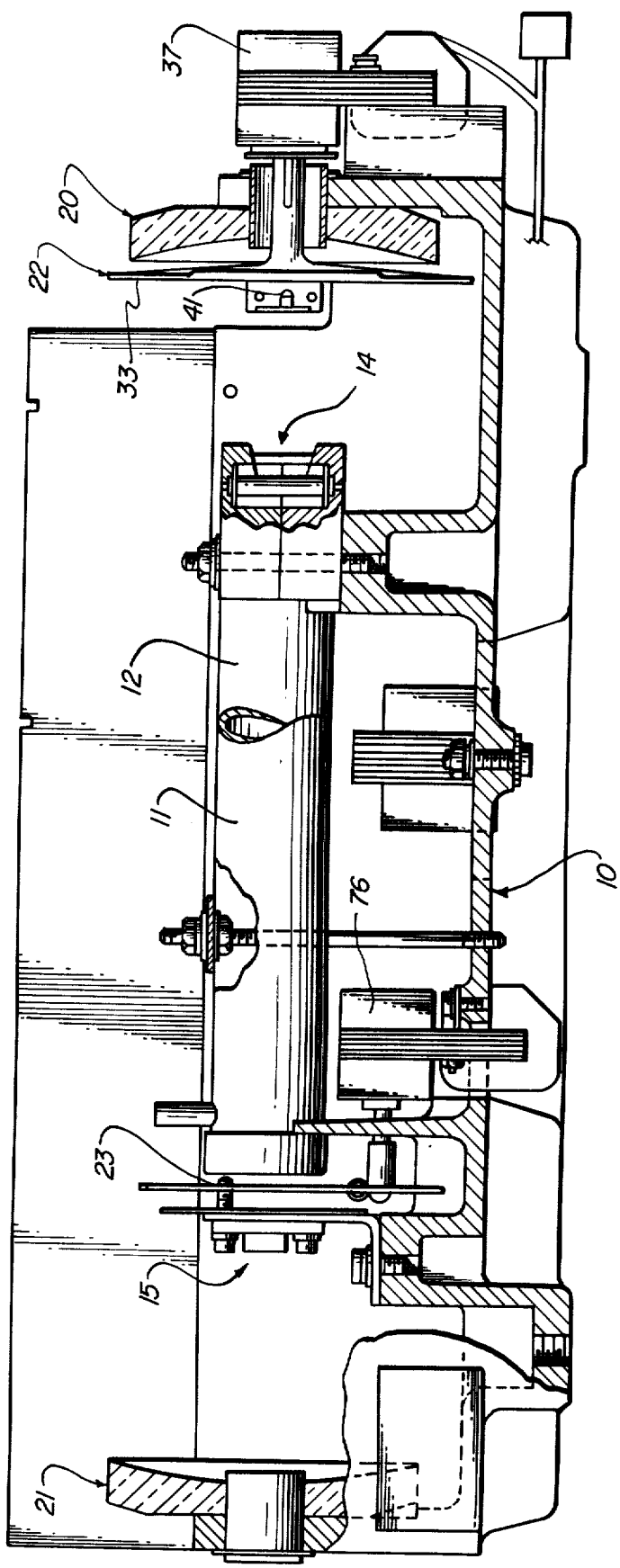
FIG. 3 is a sectional view of the optical bench portion of the gas analyzer; taken along lines 3—3 of FIG. 2.
Figure 4:
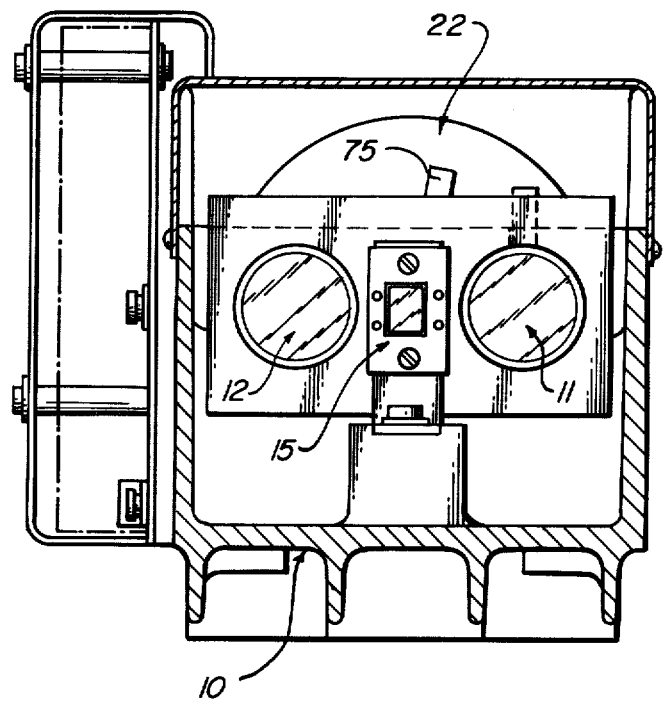
FIG. 4 is a sectional view of the optical bench taken along lines 4—4 of FIG. 2.

Referring now to the drawings, in FIGS. 2, 3 and 4, the optical bench portion of a multiple gas analyzer utilizing the infrared absorption principle for determining the quantity of two or more gases in a sample is shown. The gas analyzer includes as its principal components a frame 10 upon which are supported a sample tube 11, a reference tube 12, an infrared source 14, an infrared detector assembly 15, a transmitting mirror 20, a receiving mirror 21, a chopper disc and motor assembly 22, and a calibration flag and motor assembly 23. Associated with the optical bench of the gas analyzer are readout meters 24 and 25 (FIG. 6) in circuit relationship with the infrared detector assembly 15, for determining the quantity of various gases in a sample gas, all as more fully described below.

More particularly, the gas analyzer includes a pair of parallel tubes, one being the sample tube 11 through which the sample gas is pumped, and the other being the reference tube 12 in close parallel relationship to the sample tube 11. The reference tube 12 is filled with ambient air although it can be sealed and even reduced to a vacuum. The infrared source 14 is positioned between and adjacent the ends of the sample tube 11 and reference tube 12, while the infrared detector assembly 15 is similarly positioned at the opposite end of the sample and reference tubes.

As can be seen in FIGS. 2-4, and particularly 5, the infrared beams generated by the infrared source 14 impinge on the transmitting mirror 20, and the latter is located and concavely configured to reflect the infrared beams back through the sample tube 11 and the reference tube 12, onto the receiving mirror 21. The receiving mirror 21 likewise is located and concavely configured to reflect the infrared beams onto the infrared detector assembly 15. The chopper disc 33 is provided between the infrared source 14 and the transmitting mirror 20 to alternately reflect the infrared beams through the sample tube 11 and the reference tube 12. The arrangement also is such that the infrared beams are alternately impinged on the various infrared detectors supported by the detector assembly 15. The infrared detectors are coupled to readout meters, such as the readout meters 24 and 25 shown in FIG. 6, through circuit means arranged to compare the signals received by individual ones of the infrared detectors when passing through the sample tube 11 and reference tube 12, respectively. The difference in the two signals is displayed by the readout meter, with the circuit means and the readout meter being calibrated such that the readout is an indication of the concentration of a particular gas in the sample.

In the illustrated embodiment, the gas analyzer is arranged for detecting and determining the quantity of concentration of two different gases, namely, carbon monoxide (CO) and unburned hydrocarbons (HC). From the description below, however, it will be apparent that the gas analyzer can be arranged to determine the concentration of additional gases, such as nitric oxide (NO) and other similar gases, simply by providing the necessary infrared detectors and filters in the focal plane of the transmitting and receiving mirrors 20 and 21, so that the infrared beams are impinged on them, as more particularly described below.

In a particular application, the choice of infrared detectors depends on the spectral signature of the gas to be analyzed. In the illustrated embodiment, lead selenide (PbSe) detectors are used to detect both the CO and the HC. As the infrared beams travel from the infrared source 14 through either the sample gas or air, the irradiance at the infrared detector will be proportional to the transmission of the medium over a specific narrow spectral range which is selected as the most favorable signature of the constituent gas component in the sample gas. To provide this narrow spectral window, a filter 27 (FIG. 10) is placed over the infrared detector. These filters, in this particular application are a silicon substrate having a 4.70 micron wavelength and a bandwidth of $0.2\mu \pm 0.05$ for the CO detector, and a water free quartz substrate having a 3.45 micron wavelength and a bandwidth of $0.15\mu \pm 0.05$ for the CO detector, and a water free quartz substrate having a 3.45 micron wavelength and a band width of $0.15\mu \pm 0.05$ for the HC detector.

The infrared detector assembly 15 is shown in FIGS. 8, 9 and 10, and can be seen to include a bracket 28 for securing it to the frame 10 of the gas analyzer. The bracket 28 supports a CO detector-filter assembly 29 and a HC detector filter assembly 30, with the CO and HC detectors being vertically aligned and in close proximity to one another. As can be best seen in FIG. 10, the filters are supported in front of the detectors, and electrical connections are established from the detectors to a pair of connector terminals 31 and 32, for coupling the detectors to the circuit means described more fully below. The layout or arrangement of the detectors is important to the invention in that they must be disposed in a position such that the infrared beams can be impinged on each of them, whether detecting two or more gases. While the detectors, in the illustrated embodiment, are vertically disposed, they could as well be horizontally or otherwise disposed.

The infrared source 14 can be a conventional source which will emit radiation and, in the illustrated embodiment, the infrared source is operated at approximately 1100°K.

In FIGS. 11 and 12, the chopper disc 33 interposed between the infrared source 14 and the transmitting mirror 20 is shown, and it can be seen to be generally circular-shaped, with a 45° arcuate-shaped sync slot 34 formed in its peripheral edge. Diametrically opposed to the sync slot 34 is a modulator slot 35 which is generally arcuate-shaped. The modulator slot 35 is spaced inwardly from the peripheral edge of the chopper disc 33, and extends approximately 105°. The chopper disc 33 can be formed of black nylon with a matte finish. A hub 36 is provided for affixing it to the shaft of an AC motor 37 (FIG. 2). The chopper disc 33 is rotated by the motor 37, at a speed of approximately 3000 rpm.

Figure 5:
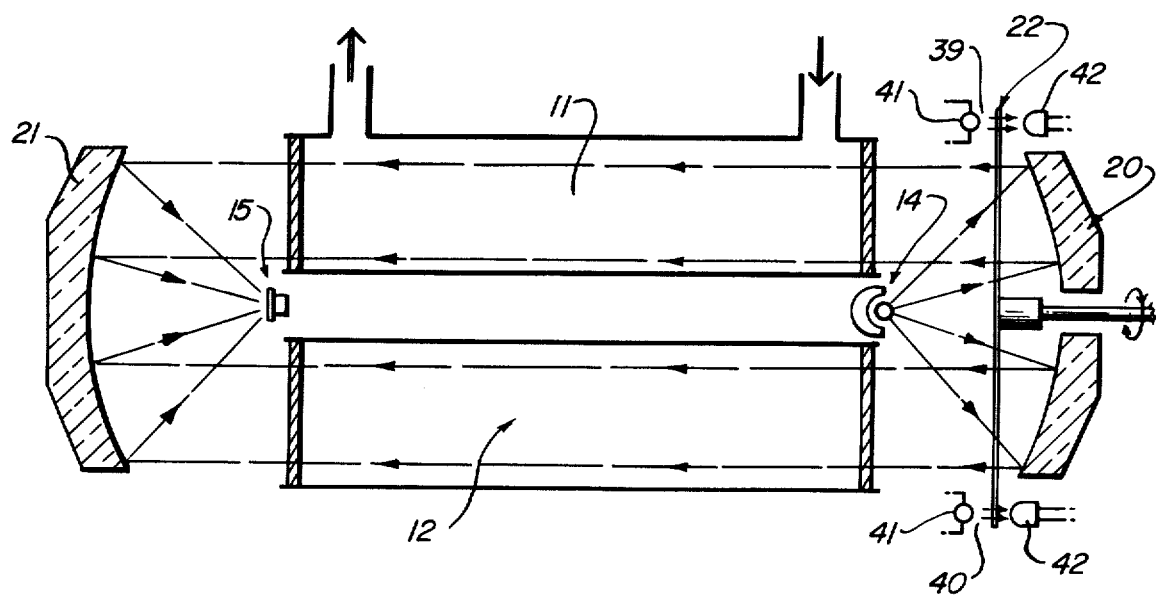
FIG. 5 is a plan view generally illustrating the manner in which the infrared beam is reflected through the sample and reference tubes.

In FIGS. 2 and 5, it can be seen that a pair of sync light assemblies 39 and 40 are supported on the frame 10 of the gas analyzer in operative relationship with the chopper disc 33, and more particularly, with the sync slot 34 therein, to provide output sync pulses as the chopper disc 33 rotates. These sync light assemblies each may be formed of a light emitting diode 41 and a phototransistor pickup 42 diposed on opposite sides of the chopper disc 33, such that the light from the light emitting diode 41 impinges on the phototransistor 42 only when the sync slot 34 is positioned between them. These sync light assemblies 39 and 40 are illustrated in dotted lines in FIG. 11, as are the ends of the sample tube 11 and reference tube 12. The arrangement is such that the modulator slot 35 is disposed in front of the reference tube 12 when the sync slot 34 is disposed in front of its associated sync light assembly 39, so that a sync pulse is generated each time the modulator slot 35 is positioned to permit the infrared beams to pass through the reference tube 12. The sync light assembly 40 is associated with the sample tube 11, and is correspondingly positioned to generate a sync pulse when the modulator slot 35 is positioned to permit the infrared beams to pass through the sample tube 11.

In FIGS. 13, 14 and 15, the relationship between the reference sync pulse, the sample sync pulse and the times the sample and reference tubes are exposed are shown. It can be seen that the sample tube and the reference tube both are exposed for 165° of rotation of the chopper disc 33, and that there is a dead zone of the 15° of rotation between them. The sync pulses are generated at the times that the sample and reference tubes are fully exposed, that is, for example, in the case of the sample tube 11, when it has rotated 60° and until it has rotated 105°.

Referring now to FIGS. 5 and 6, the manner in which the detector outputs and the sync pulses are used in determining the quantity of HC or CO in a gas sample can be described. As the chopper disc 33 rotates, the infrared beams are alternately reflected through the sample tube 11 and the reference tube 12, onto the HC and the CO detectors. The infrared beams from the lower part of the infrared source 14 are reflected onto the upper or HC detector, while the infrared beams from the upper part thereof are reflected onto the lower or CO detector. This arrangement provides for comparing the absorption of two gases simultaneously.

In FIG. 6, with reference to the HC detector, its output signals are coupled to a pre-amplifier 44 which may be a two-stage AC coupled amplifier with a high input impedance. From the pre-amplifier 44, the composite signal resulting from the infrared beams passing through the sample tube 11 and the reference tube 12 is coupled to a gain control circuit 45. The output of the gain control circuit 45 is clamped to common by means of a switch transistor (not shown) during each reference sync pulse which is coupled to the switch transistor via the sync pickup and amplifier 49 to yield a clamped and amplitude stabilized composite signal at the output of the reference clamp 46. The AGC control 47 is adjusted for a 1 volt PP signal to allow the AGC a greater dynamic range in the presence of temperature induced changes in detector signal output. Another switch transistor (not shown) at the output of the reference clamp 46 samples the composite signal during each sample sync pulse which is coupled to it via the sync pickup and amplifier 50. The sampled signal level is stored in an integrating capacitor (not shown), and coupled to an output integrator 48 which is a signal gate and amplifier with zero and span control suitable for driving an indicator such as the meter 24. The sampled composite signal level is a signal proportional to the absorption of the infrared beam by the medium through which the beams were passed and, in view of the HC filter, is related to the spectral signature of HC, hence it is a measure of the concentration of HC in the sample gas. The output signals from the CO detector are similarly sampled, to obtain a sampled composite signal level proportional to the concentration of CO in the sample gas.

Figure 7:
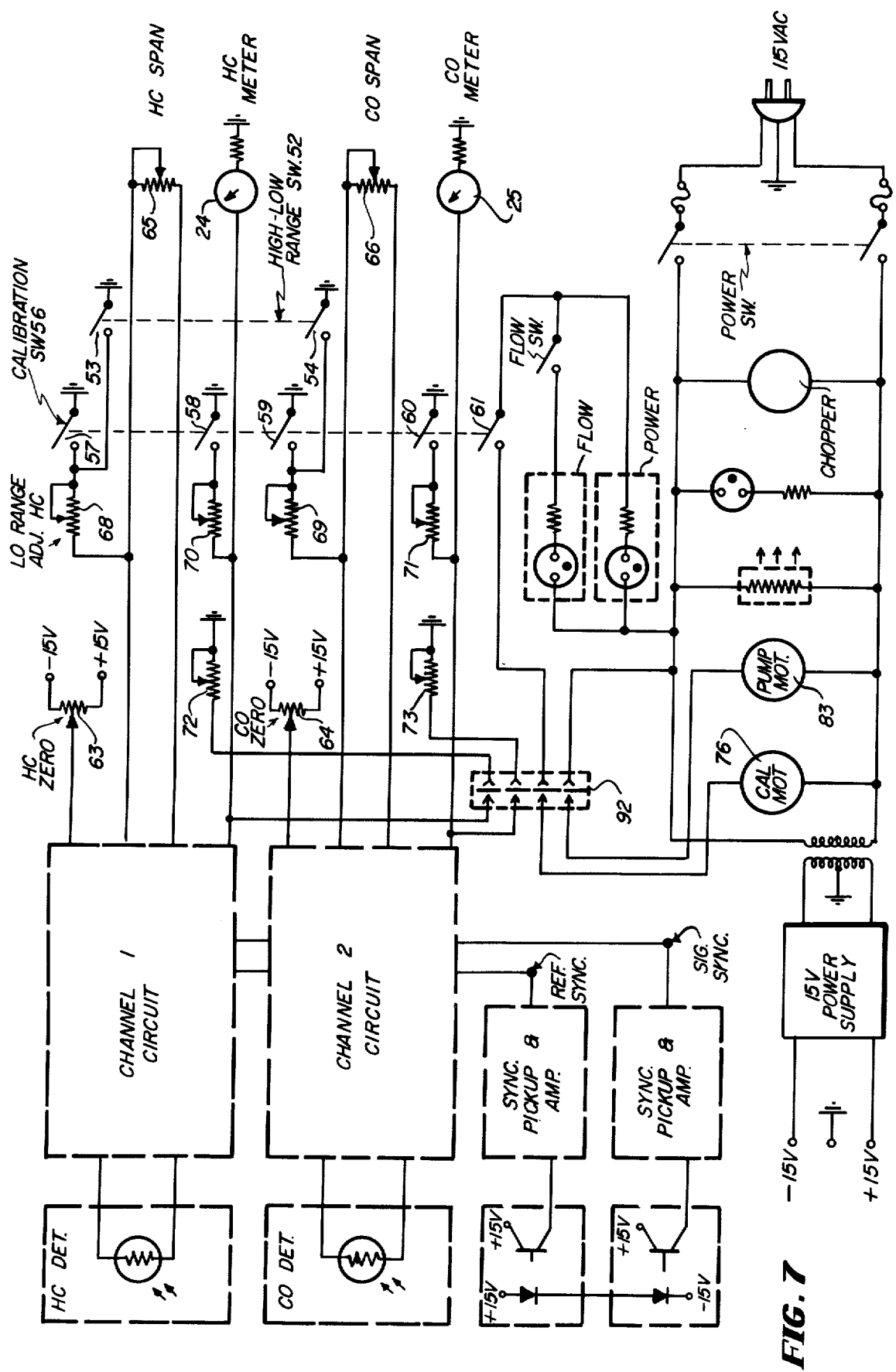
FIG. 7 is a schematic further illustrating the circuit means of the gas analyzer.

In FIG. 7, the calibration adjustments for the gas analyzer are shown. The gas analyzer initially is factory calibrated with span gases of known concentration, by filling the sample tube 11 with the span gas. The HIGH-LOW range switch 52 is set to its HIGH position, so that contacts 53 and 54 are open. At this time, the contacts 57–61 of the calibration switch 56, more particularly described below, also are open. The ZERO adjustment controls 63 and 64, and the SPAN adjustment controls 65 and 66 are adjusted to properly zero and to set the range of the meters 24 and 25. During this adjustment a span gas having a high concentration substantially corresponding to the maximum concentrations expected to be analyzed preferably is used, so that the meters are capable of reading such concentrations of HC and CO. In calibrating the gas analyzer in the LOW range, the sample tube 11 is filled with a span gas of a known low concentration, and the calibration switch 56 is switched to close its contacts 57–61. These contacts switch in respective ones of the trimmer resistors 68–71, to permit fine adjustments to be made to properly calibrate the gas analyzer's circuitry and meters.

It has been found that in calibrating the gas analyzer using span gases of known concentrations, when actual exhaust gases are analyzed, there is a slight variation in the readings indicated by the readout meters 24 and 25. The reason for this is the presence in the exhaust gas of several constituents which differ slightly from the spectral signatures of the pure gases, but whose contributions are conventionally included in the total measurement. Accordingly, after pre-calibrating the gas analyzer in the above-described fashion, an exhaust gas is passed through the sample tube 11, and the trimmer resistors 72 and 73 are adjusted to compensate for the variation in readings for the span gases and the exhaust gases. The adjustments of the trimmer resistors 67–73 all are factory adjustments to calibrate the gas analyzer, and thereafter the only adjustments made by the operating personnel are the ZERO and SPAN adjustment controls 63, 64, 65 and 66, with these adjustments being made upon energizing the gas analyzer and prior to conducting any tests. The trimmer resistors 72 and 73 also are arranged to be removed from the circuitry during subsequent calibrations of the gas analyzer, as more fully discussed below.

The gas analyzer also includes a calibration flag and motor assembly 23 which is used by the operating personnel for calibrating it upon being energized and prior to conducting tests. This calibration flag and motor assembly 23, as can be best seen in FIGS. 16 and 17, includes a calibration flag 75 which is an opaque paddle secured for rotation to the shaft 77 of a shaded pole motor 76. A return spring 78 is affixed to the calibration flag 75 and to a support bracket (not shown) for returning the calibration flag 75 to an inoperative position when not in use. The calibration flag and motor assembly 23 is supported upon the frame 10 of the gas analyzer, and is positioned such that the calibration flag 75 is rotated against a stop 79, into the optical path for partial obscuration of the infrared beams through the sample tube 11 in simulation of span gas. The motor 76 is energized through the contact 61 of the calibration switch 56, when the latter is operated. The contacts 57 and 59 of the calibration switch 56 likewise are closed when the latter is operated, to place both the HC and CO channels of the gas analyzer into the LOW range, overriding the range switch 52. Upon releasing the calibration switch 56, its contacts all automatically restore to an open position, and the latter motor 76 is de-energized. The return spring 78 rotates the calibration flag 75 to its normally inoperative position. Accordingly, it can be seen that the gas analyzer can be easily and quickly calibrated in the field, simply by operating the calibration switch 56 and by adjusting the ZERO and SPAN adjustment controls 63–66.

Figure 1:
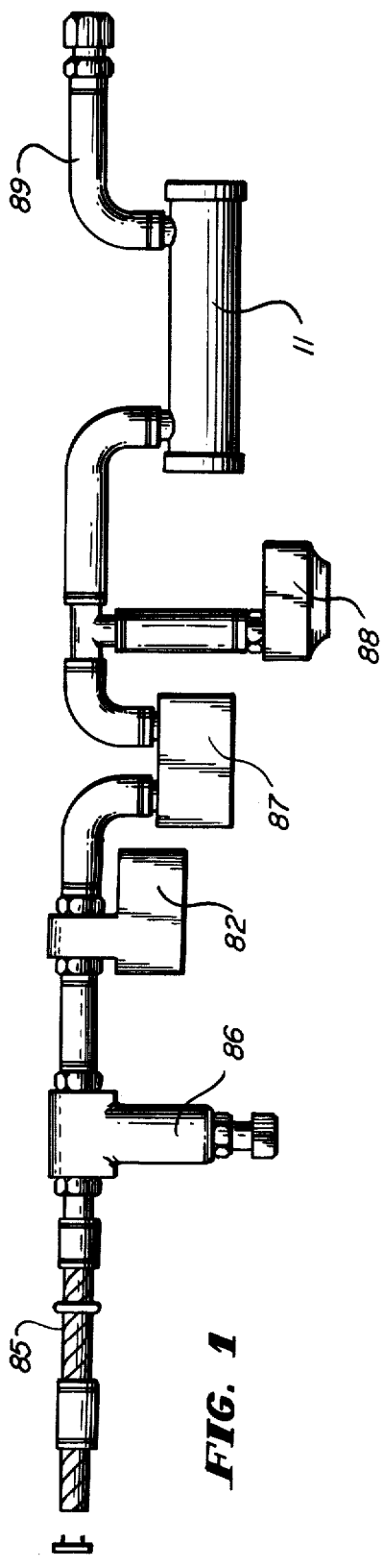
FIG. 1 is a view generally illustrating the flow path of the sample gas to the sample tube, through the filter, pump, condenser and flow switch.

During normal testing operations, the sample gas is pumped through the sample tube 11 of the gas analyzer, at a flow rate of approximately 20 cubic feet per hour. For this purpose, a pump 82 (FIG. 1) driven by a motor 83 (FIG. 7) is provided. The motor 83 is energized and runs continuously as long as the gas analyzer is energized, thus the pump 86 runs continuously. In most cases, and particularly in testing automotive exhaust gases, the sample gas is filtered, cooled and dried before being passed through the sample tube 11. Accordingly, as can be seen in FIG. 1, a pickup hose 85 is provided for picking up the sample gas and, in the case of an exhaust gas, the pickup hose 85 is adapted to be extended into the tail pipe of a vehicle. The gas then is passed through a filter 86 to the pump 82. From the pump 82, the gas passes through a condenser 87 and a flow switch 88 to the input of the sample tube 11. Water removed from the gas by the condenser 87 drains therefrom through a drain hole or holes in the bottom end thereof. From the sample tube 11, the gas is exhausted through the outlet hose 89. In a specific application, the above-described flow path for the sample gas has built-in leaks so that only approximately 20 percent of the sample gas actually is passed through the sample tube 11. The flow switch 88 is a pressure switch which indicates flow to the sample tube.

During initial factory calibration with span gases, the motor 83 is de-energized and hence the pump 82 stopped, by disconnecting the source of power to the motor 83. This allows using just enough span gas to fill the sample tube 11, and avoids pumping and wasting large volumes of calibrated gases. Also, as indicated above, the trimmers 72 and 73 are arranged to be disconnected from the circuitry during subsequent calibrations of the gas analyzer with span gases. This is to prevent individuals other than factory authorized personnel from upsetting these previously set trimmer resistors which compensate for the difference in meter readings in testing span gases and actual sample gases such as exhaust gas. This is accomplished by connecting these resistors through a terminal or junction block 92, the energizing circuits for the pump motor 83 and the motor 76 of the calibration flag and motor assembly 23 likewise are connected through this junction block 92. By unplugging the junction block 92, the sample tube 11 can be filled with a span gas for calibrating the gas analyzer, and will not be pumped through it since the energizing circuit for the pump motor 83 is opened. The calibration flag 75 is not used during the calibration, hence its motor 76 likewise is opened when the junction block 92 is unplugged. It may also be seen that the trimmer resistors 72 and 73 are taken out of the circuit and thus will have no effect when subsequent calibrations are made. Accordingly, the net effect is that the gas analyzer is re-calibrated with the span gas, but as soon as the junction block 92 is plugged in again, the trimmer resistors 72 and 73 are connected back into circuit relationship and provide the necessary compensating values for other exhaust gases.

From the above description, it can be seen that once factory calibrated, the gas analyzer can be easily recalibrated prior to use, or during use, to correct for any variations due to drift or temperature variations, simply by operating the calibration switch 56 and making the appropriate adjustments. Furthermore, the gas analyzer is capable of providing simultaneous indications of two constituents such as HC and CO of a sample gas, hence it is particularly applicable for testing sutomotive emissions to determine whether they comply with set standards. The gas analyzer further has been found to have a fast warm up time, and to provide relatively constant readings so that it does not have to be continuously tuned or calibrated. Further still, it is relatively inexpensive in comparison to existing gas analyzers and is readily portable.

It will thus be seen that the objects set forth above, among those made apparent from the preceding description, are efficiently attained and certain changes may be made in the above construction. Accordingly, it is intended that all matter contained in the above description or shown in the accompanying drawings shall be interpreted as illustrative and not in a limiting sense.

Now that the invention has been described, what is claimed as new and desired to be secured by Letters Patent is:

1. A gas analyzer of the infrared absorption character comprising, in combination, a frame, a sample tube, a reference tube, said sample and reference tubes both being supported by the frame, an infrared source positioned at one end of the tubes, a detector means comprising a plurality of detectors and a filter over each of said detectors appropriate to a component to be analyzed positioned at a spot remote from the infrared source, a transmitting mirror remote from the infrared source and said tubes proportioned optically to receive, to split, and to image the split parts of the infrared beam back through each the sample tube and the reference tube in substantially equal intensity, a receiving mirror remotely opposed to said transmitting mirror and opposite the detector means optically proportioned to direct the respective imaged split parts of the infrared beam from said tubes toward the respective ones of said plurality of detectors, the path lengths of said infrared beam from said infrared source to said sample tube and to said reference tube and from said sample tube and said reference tube to said detector means being identical and the length of said sample and reference tubes being identical, and wherein all elements of the optical system are identical, whereby the optical system of said gas analyzer is completely balanced, chopper means interposed in said pathway between the infrared source and detector means to alternatively direct the path of the imaged parts of the infrared beam through the sample tube and reference tube so apertured that energy never passes through both tubes simultaneously but rather passes through each tube for less than one half the time for one rotation of the chopper means thereby alternately gating energy through the reference tube and the sample tube with a time gap therebetween, and readout means in circuit relationship to each of said detectors to compare the signal attenuation through the sample chamber with the reference chamber and calibrate the same to read the concentration of gas specific to the wave length of the detector's associated filter proportional to the signal differential between the reference tube and the sample tube, thereby enabling the gas analyzer to read out two or more components simultaneously without time sharing, said readout means in circuit relationship to each of said detectors comprising, amplifier means for amplfying the output signal from said detector, gain control means directly coupled to said amplifier means, a reference clamp for clamping to ground the output signal during the time the infrared beam passes through the reference tube, an automatic gain control amplifier for providing a peak-to-peak signal of a pre-established value, the clamped and amplitude stabilized signal from said gain control means and said reference clamp being coupled to said automatic gain control amplifier, means for sampling the signal amplitude as said infrared beam passes through said sample tube, means for storing said sampled output, and means for coupling said stored sampled output to meter means for indicating the variation in signals between said reference tube and said sample tube from the same detector as the copper alternately directs signals through each of said tubes.

2. In the gas analyzer of claim 1,
said chopper means being positioned between the infrared source and the transmitting mirror.

3. In the gas analyzer of claim 1 said detectors are aligned in close proximity one to another, and the related filters are positioned in close proximate relationship to each detector.

4. In the gas analyzer of claim 1,
vignetting means positionable to a stationary position to interrupt the path of radiation from said source through the sample chamber, said vignetting means being proportioned to a desired full meter reading equivalent to the concentration of the particular gas involved thereby simulating the photon absorption of that particular gas as the same passes through the sample tube, whereby said gas analyzer is provided with means for calibrating the same to full meter strength, based upon a simulation of a known standard span gas.

5. In the gas analyzer of claim 1, each of said meter means comprising, means providing for a high range scale reading and a low range scale reading, switch means for presetting the meter for the high range or low range scale reading, an adjustment means on the low range scale reading whereby, when a particular reading is observed on the high range scale reading, the low range scale reading may be switched into operation, and calibrated to read the same reading as noted on the high range scale reading.

6. In the gas analyzer of claim 5,
the ratio between the high range and low range scale readings being two to one.

7. In the gas analyzer of claim 1, further including trimmer resistance means for calibrating said readout means to compensate for variations in the readings thereof for span gases and exhaust gases, whereby the presence in the exhaust gases of several constituents which differ slightly from the spectral signatures of the pure span gases but whose contributions are conventionally included in the total measurement can be compensated for when actual exhaust gases are analyzed.

8. In the gas analyzer of claim 7, wherein said trimmer resistance means are arranged to be disconnected from circuit relationship with said readout means during calibration of the gas analyzer using span gases.

9. In the gas analyzer of claim 7, pump means for positively directing the exhaust gas through the sample tube, said pump means arranged to be rendered inoperative during calibration of the gas analyzer using span gases, said trimmer resistance means being arranged to be automatically disconnected from circuit relationship with said readout means when said pump means is rendered inoperative.

* * * * *